United States Patent [19]

Sih

[11] Patent Number: 4,619,997
[45] Date of Patent: Oct. 28, 1986

[54] SUBSTITUTED 2-PYRIDYLMETHYLTHIO AND SULFINYL-BENZIMIDAZOLES AS GASTRIC ANTISECRETORY AGENTS

[75] Inventor: John C. Sih, Kalamazoo, Mich.

[73] Assignee: The Upjohn Company, Kalamazoo, Mich.

[21] Appl. No.: 812,224

[22] Filed: Dec. 23, 1985

Related U.S. Application Data

[60] Division of Ser. No. 648,118, Sep. 6, 1984, Pat. No. 4,575,554, which is a continuation-in-part of Ser. No. 558,087, Dec. 5, 1983, abandoned.

[51] Int. Cl.$^4$ .................. C07D 401/14; C07D 413/14
[52] U.S. Cl. ..................................... 544/124; 544/131
[58] Field of Search ...................... 544/124, 131, 364; 546/193, 271

[56] References Cited

U.S. PATENT DOCUMENTS

| | | | |
|---|---|---|---|
| 4,045,563 | 8/1977 | Berntsson et al. | 546/271 |
| 4,255,431 | 3/1981 | Junggren et al. | 546/271 |
| 4,337,257 | 6/1982 | Junggren et al. | 546/271 |
| 4,359,465 | 11/1982 | Ruwart | 546/271 |

FOREIGN PATENT DOCUMENTS 2134523  8/1984  United Kingdom .

*Primary Examiner*—Robert W. Ramsuer
*Attorney, Agent, or Firm*—Lawrence T. Welch

[57] ABSTRACT

The present invention provides substituted 2-pyridylmethylthio- and sulfinyl-benzimidazoles with gastric acid inhibiting effects.

2 Claims, No Drawings

SUBSTITUTED 2-PYRIDYLMETHYLTHIO AND SULFINYL-BENZIMIDAZOLES AS GASTRIC ANTISECRETORY AGENTS

CROSS REFERENCE TO RELATED APPLICATION

This application is a division of copending Ser. No. 648,118, filed Sept. 6, 1984, now U.S. Pat. No. 4,575,554, which is a continuation-in-part of copending application Ser. No. 558,087, filed Dec. 5, 1983, now abandoned.

BACKGROUND OF THE INVENTION

The present invention involves novel compositions of matter. More particularly, the present invention involves novel substituted 2-pyridylmethyl-thio and -sulfinyl benzimidazoles which are useful as gastric antisecretory and cytoprotective agents.

Gastronintestinal inflammatory diseases are characterized by inflammation, specifically by the presence of edema, characteristic inflammatory cells (i.e., leukocytes, histiocytes, and macrophages), and, in some cases, necrosis and ulceration of the surface epithelium. These inflammatory diseases are known to be caused by a wide variety of agents present in the gastrointestinal tract which are known to attack the surfaces thereof, producing the inflammatory disease response. Such agents include micro-organisms (viruses and fungii), bacterial toxins, certain pharmaceutical agents (antibiotics and antiinflammatory steriods), and chemical agents (bile salts, toxic household chemicals). Gastric acid itself is also capable of attacking the stomach lining and producing an inflammatory state.

One means of preventing or treating certain gastrointestinal diseases, specifically gastric diseases, is by the inhibition of gastric acid secretion. In situations where the integrity of the gastric mucosal barrier is compromised, gastric acid secretion can result in erosion of the epithelial cells with consequent inflammation and ulceration. Inhibition of such untoward gastric acid-induced effects can be achieved by the administration of a pharmacological agent effective to inhibit gastric secretion.

One class of such agents effective to inhibit gastric acid secretion are the gastric antisecretory prostaglandins. These substances are known to be effective in the treatment and care of gastric and duodenal ulcers as a result of the inhibition of gastric secretion. See, e.g., U.S. Pat. No. 3,903,297 (Robert, "Method of Treatment and Prophylaxis of Gastric Hypersecretion and Gastric Duodenal Ulcers Using Prostaglandin Analogs"), and Robert, "Antiscretory Property of Prostaglandins," Prostaglandin Symposium of the Worcester Foundation for Experimental Biology 16–17 October 1967, Interscience, New York, page 47 (1968). Another important class of antisecretory agents are the histamine $H_2$ receptor antagonists, including metiamide and most importantly cimetidine, N-cyano-N'-methyl-N''[2-[[(5-methyl-1H-imidazole-4-yl)methyl]thio]thio]ethyl]guanidine. See, the Merck Index, 9th Edition, Appendix, page App-1 (1976), and Physcan's Desk Reference, 36th Edition, 1812–1814 (1982).

Another means of treating such gastrointestinal diseases is through cytoprotection. Certain pharmacological agents have heretofore been known to be useful in exerting a cytoprotective effect on the gastrointestinal tract. This cytoprotective effect is manifest in the ability of such compounds to treat or prevent non-traumatically-induced, non-neoplastic inflammatory disease of the gastrointestinal tract. References describing such cytoprotective effects of prostaglandins are U.S. Pat. No. 4,083,998 (Robert, "Treatment of Inflammatory Diseases of the Mammalian Large Intestine with Cytoprotective Prostaglandins"), issued Apr. 11, 1978; U.S. Pat. No. 4,081,553 (Robert, "Cytoprotective Prostaglandins for Use in Intestinal Diseases"), issued Mar. 28, 1978; and U.S. Pat. No. 4,097,603 (Robert, "Gastric Cytoprotection with Non-Antisecretory Doses of Prostaglandins"), issued June 27, 1978. Gastric cytoprotection is a distinct pharmacological property which is unrelated to gastric antisecretory effects. See, e.g., Robert, U.S. Pat. No. 4,097,603, "Gastric Cytoprotection With Non-Antisecretory Doses of Prostaglandins," Robert, "Cytoprotection by Prostaglandins," Gastroenterology 77:761–767 (1979); Robert, "Current History of Cytoprotection," Prostaglandins 21 (supp):89 (1981), and Robert, et al., "Cytoprotection by Prostaglandins in Rats," Gastroenterology, 77:433–443 (1979). Thus, compounds which are gastric anti-secretory agents may not be cytoprotective agents and vice-versa.

PRIOR ART

U.S. Pat. No. 4,045,563 discloses certain substituted 2-[pyridylalkylenesulfinyl]-benzimidazoles having gastric acid secretion inhibiting effects. U.S. Pat. No. 4,255,431 discloses certain 2-(2-benzimidazolyl)-pyridines which are useful in inhibiting gastric secretion. U.S. Pat. No. 4,337,257, discloses some additional 2-(2-benzimidazolyl)-pyridines which are useful in inhibiting gastric secretion. Finally, U.S. Pat. No. 4,359,465 discloses the cytoprotective use of certain heterocyclylalkylsulfinylbenzimidazoles.

SUMMARY OF THE INVENTION

The present invention particularly provides: a compound of the Formula I,
wherein X is
  (a) =S, or
  (b) =SO;
wherein $R_1$ is
  (a) hydrogen,
  (b) methyl,
  (c) methoxy, or
  (d) trifluromethyl; p0 wherein $R_2$ is
  (a) —$SR_5$,
  (b) —$OR_5$,
  (c) —$N(R_4)_2$
  (d) 1-piperidinyl,
  (e) 4-morpholinyl,
  (f) 4-methyl-piperazin-1-yl, or
  (g) 1-pyrrolidinyl;
wherein $R_5$ is
  (a) ($C_1$–$C_4$)alkyl,
  (b) ($C_1$–$C_4$)alkenyl,
  (c) PhX,
  (d) —$CH_2$—PhX, or
  (e) ($C_4$–$C_{10}$)cycloalkyl;
wherein (PhX) is phenyl substituted by zero to 3 of the following:
  (a) ($C_1$–$C_4$)alkyl,
  (b) chloro,
  (c) fluoro,
  (d) bromo,
  (e) nitro,
  (f) trifluoromethyl; or (g) OR$_3$;
wherein R$_3$ and R$_4$ are the same or different and are
(a) hydrogen, or
(b) (C$_1$-C$_4$)alkyl;
with the proviso that when R$_2$ is —OR$_5$, and R$_5$ is (C$_1$-C$_4$)alkyl, R$_3$ is other than hydrogen or methyl.

The carbon atom content of various hydrocarbon-containing moieties is indicated by a prefix designating the minimum and maximum number of carbon atoms in the moeity, i.e., the prefix (C$_i$-C$_j$) indicates a moiety of the integer "i" to the integer "j" carbon atoms, inclusive. Thus (C$_1$-C$_4$) alkyl refers to alkyl of one to 4 carbon atoms, inclusive, or methyl, ethyl, propyl, butyl, and isomeric forms thereof.

Examples of (C$_3$-C$_{10}$)cycloalkyl which include alkyl-substituted cycloalkyl, are cyclopropl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, 2,3,4-triethylcyclobutyl, cyclopentyl, 2,2-dimethylcyclopentyl, 2-pentylcyclopentyl, 3-tert-butylcyclopentyl, cyclohexyl, 4-tert-butylcyclohexyl, 3-isopropylcyclohexyl, 2,2-dimethylcyclohexyl, cycloheptyl, cyclooctyl, cyclonoyl and cyclodecyl.

Examples of (C$_2$-C$_4$)alkenyl include 1-propenyl, 3-butenyl and isomeric forms thereof.

Examples of PHX include phenyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4-, 2,3,6-, or 2,4,5-)trimethylphenyl, (o-, m-, p-)fluorophenyl, (o-, m-, or p-trifluoromethyl)-phenyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3,5-xylyl, (2,3-, 2,4- 2,5- 2,6- or 3,5-)dichlorophenyl, 4-chloro-3-fluorophenyl, (3- or 4-)chloro-2-fluorophenyl, (o-, m-, or p-)trifluoro-methylphenyl, (o-, m-, or p-)ethoxyphenyl, (4- or 5-)chloro-2-methoxy-phenyl, and 2,4-dichloro(5- or 6-)methylphenyl.

The compounds of the present invention will be namd herein using the Chemical Abstracts numbering system (see Naming and Indexing of Chemical Substances for Chemical Abstracts during the Ninth Collective Period (1972-1976), a reprint of section IV from the Volumn 76 Index Guide.)

Compounds of this invention have been tested in one or more standard laboratory tests which demonstrate gastric antisecretory activity. Thus, compounds of this invention have been shown to be effective as inhibitors of K$^+$—dependent ATP hydrolysis by isolated hog gastric membranes enriched with gastric(H$^{30}$-K$^+$)ATPase. In this system, 2-[(4-methoxy-3-ethylpyridin-2-ylmethyl)sulfinyl]-benzimidazole has been shown to be the most effective with an ID$_{50}$ of $3 \times 10^{-6}$M. In a test for in vivo inactivation of (H$^+$-K$^+$)ATPase in the rat, 2-[(4-ethylthio-3-methylpyridin-2-ylmethylsulfinyl]-benzimidazole was shown to be the most effective, having an ED$_{50}$ of 1 mg/kg. Compounds of this invention have been shown to be active as inhibitors of acid secretion in isolated gastric glands of the rabbit. In this system, 2-[(4-ethylthio-3-ethylpyridin-2-ylmethyl)sulfinyl]-benzimidazole was shown to be the most effective with an ID$_{50}$ of $1 \times 10^{-7}$M.

A significant advantage of certain of the compounds of the instant invention, particularly those of the Formula I wherein R$_1$ is hydrogen, X is =S(O), R$_3$ is methyl or ethyl, R$_4$ is hydrogen, and R$_2$ is methylthio, ethylthio, or propylthio, is their long duration of activity when administered subcutaneously. Thus, even after 6 days 2[(4-ethylthio-3-ethylpyridin-2-ylmethyl)sulfinyl]-benzimidazole and 2-[(4-ethylthio-3-methylpyridin-2-ylmethyl)sulfinyl]-benzimidazole inhibited gastric acid secretion in the rat 68 and 82%, respectively, when administered subcutaneously at a dose of 50 mg/kg.

As noted, all of the compounds of this invention are useful as gastric antisecretory agents.

Compounds of this invention are administered for gastric antisecretory purposes orally, parenterally, (e.g., intravenously, subcutaneously, intramuscularly or intraparenterally), intradermally, rectally, or vaginally in forms such as pills, capsules, solutions, suspensions, suppositories, or bougies. The compounds of this invention are formulated into these pharmaceutical compositions by means known to the pharmaceutical art.

An ordinarily skilled physician can readily determine persons suffering from gastrointestinal diseases characterized by the gastric-acid induced effects noted above. These conditions are treated using the compounds of the present invention.

Typical dose ranges for the compounds of this invention range from about 0.01 µg per kg to about 250 mg per kg, preferably from about 0.1 to 100 mg per kg. The choice of the use, route, and frequency of administration of the compounds of this invention depends on the weight, age, and gastrointestinal disease of the patient and the particular compound employed. These decisions are readily made by a physician or ordinary skill in the art.

However, to achieve a longer duration of action, these compounds are administered subcutaneously. This is the preferred route for administering the class of compounds noted above having this property, when the therapeutic objective requires it. However, when a long duration of action is not desired, and/or the compounds lack this property, any convenient route of administration (e.g., oral) is employed.

The long duration of activity of certain of the compounds of this invention, as noted above, allows them to be used prophylactically in the treatment of patients with a high possibility of developing stress ulcerations. Further this latter class of compounds can be administered subcutaneously or intramuscularly on a weekly, biweekly, or monthly basis for the prophylaxis and/or treatment of gastric ulcer, duodenal ulcer, gastritis, esophagitis, Zollinger-Ellison syndrome, stress ulcers and upper gastrointestinal bleeding. The frequency of administration will depend on the particular compound employed as well as the dose.

The compounds of this invention may also exert cytoprotective effects. If employed for this purpose, they could be administered as described, for example, in U.S. Pat. No. 4,359,465, particularly cols. 7 and 8 thereof. The doses employed for this purpose would in general be less than those used for gastric antisecretory effects.

The compounds of the present invention are prepared by the methods depicted in Charts A-C.

In the Charts, all variables are as defined above.

In Chart A, scheme 1, a substituted α-picolyl chloride of the Formula A-2 is reacted with a 2-mercaptobenzimidazole of the Formula A-1 in the presence of a strong base (e.g., 10N sodium hydroxide). Substituted α-picolyl chloride compounds are well known, readily available compounds or may be prepared by known means, such as depicted in Chart B, as described below.

Similarly, the substituted 2-mercaptobenzimidazoles of the Formula A-1 are well known, readily available compounds or may be prepared by known means such as that depicted in Chart C as described below.

The Formula A-3 product is oxidized by known means, such as treatment with meta-chloroperbenzoic acid, to yield the Formula A-4 product. (Sodium metaperiodate may also be used, although it is less preferred.) One equivalent of sodium bicarbonate is preferably added to the reaction mixture prior to the addition of the peracid to prevent decomposition of the final product by the m-chlorobenzoic acid which is formed during the reaction.

In scheme 2 of Chart A, a benzimidazole compound of the formula A-5 (wherein M is potassium, sodium, or lithium) is reacted with the chlorinated compound of the formula A-6 to yield the formula A-4 product. The formula A-5 compounds are known and are prepared as described in U.S. Pat. Nos. 4,045,563; 4,255,431; and 4,337,257; all of which are incorporated herein by reference. The chlorinated compounds of the formula A-6 are prepared by reacting the N-oxide intermediates of Charts B-I with known chlorinating agents (e.g., $POCl_3$, $PCl_3$, and $PCl_5$).

In scheme 3 of Chart A, a chlorinated benzimidazole of the formula A-7 is reacted with the formula A-8 thiol to yield the formula A-3 product which is converted to the formula A-4 product as described above. The formula A-7 and A-8 compounds are known or may be prepared by the methods described in U.S. Pat. Nos. 4,045,563; 4,255,431; and 4,337,257, using the intermediates prepared as described herein.

In scheme 4 of Chart A, the diamino compound of the formula A-9 is reacted with the formula A-10 acid to yield the formula A-3 product which is converted to the formula A-4 product as described above. The formula A-9 and A-10 compounds are known or may be prepared as described in U.S. Pat. Nos. 4,045,563; 4,255,431; and 4,337,257; using the intermediates prepared as described herein.

The reaction of A-1 with A-2 (Chart A, scheme 1) is carried out in a manner which is known in the art in suitable, preferably polar solvents (such as methanol, dimethylsulfoxide, acetone, dimethylformamide or acetone) with the addition or exclusion of water. It is carried out for example in the presence of a proton acceptor. Examples of suitable proton acceptors are alkali metal hydroxides, such as sodium hydroxide, alkali metal carbonates, such as potassium carbonate, and tertiary amines, such as pyridine, triethylamine or ethyl diisopropylamine. The reaction temperature can be between 0° and 150° C., temperatures between 50° and 100° C., and especially the boiling point of the solvent used, being preferred.

Similar reaction conditions to those for the reaction of A-1 with A-2 are used in the reaction of A-7 with A-8 (Chart A, scheme 3) which is carried out in a manner which is known in the art.

The reaction of A-9 with A-10 (Chart A, scheme 4) is preferably carried out in polar, optionally water-containing solvents in the presence of a strong acid, for example hydrochloric acid, in particular at the boiling point of the solvent used.

The oxidation of sulfides A-3 is carried out in a manner which is known per se and under conditions with which those skilled in the art are familiar for the oxidation of sulfides to give sulfoxides. Possible oxidizing agents are all the reagents usually employed for oxidation of sulfides, in particular peroxyacids, such as for example, peroxyacetic acid, trifluoroperoxyacetic acid, 3,5-dinitroperoxybenzoic acid, peroxymaleic acid or, preferably m-chloroperoxybenzoic acid. The reaction is expediently carried out in inert solvents, for example aromatic or chlorinated hydrocarbons, such as benzene, toluene, methylene chloride or chloroform. The reaction temperature is between −70° C. and the boiling point of the solvent used, but preferably between −30° C. and +20° C. (depending on the reactivity of the oxidizing agent and the degree of dilution). The oxidation with halogens or hypohalogenites (e.g., with aqueous sodium hypochloride solution), which is carried out expediently at temperatures between 0° and 30° C. has also proved to be very advantageous.

The reaction of A-5 with A-6 (Chart A, scheme 2) is preferably carried out in inert solvents, such as those which are also usually employed for the reaction of enulate ions with alkylating agents. Examples which may be mentioned are aromatic solvents, such as benzene or toluene. The reaction temperature is as a rule between 0° and 120° C. (depending on the nature of the alkali metal atom M) preferably at the boiling point of the solvent. For example, if M represents Li (lithium) and the reaction is carried out in benzene, the boiling point of benzene (80° C.) is preferred.

Chart B depicts a method for preparing substituted α-picolyl chlorides of the Formula A-2. A substituted 2-methyl pyridine compound of the Formula B-1 (such compounds are well-known and readily available, or may be prepared by known means, see, e.g., R. A. Abramovitch and G. A. Poulton J.C.S., Section B, 901 (1969)) is treated with hydrogen peroxide in glacial acetic acid to yield the corresponding Formula B-2 N-oxide. This compound is treated with concentrated sulfuric acid and fuming nitric acid to yield the corresponding nitro compound of the Formula B-3. The nitro compound is treated with acetyl chloride to yield the corresponding Formula B-4 chloride. The Formula B-4 compound is heated with a compound of the formula $R_2H$ in the presence of sodium hydride and dimethylformamide or heated neat (when $R_2H$ is a cyclic amine) to yield the Formula B-5 compound, which is then treated with acetic anhydride to yield the Formula B-6 compound. The acyl group is removed by mild acidic hydrolysis (e.g., treatment with 10% hydrochloric acid or saponification with base (e.g., treatment with 25% sodium methoxide in methanol)) to yield the Formula B-7 alcohol. This alcohol is then treated with methanesulfonyl chloride and triethylamine to yield the corresponding substituted α-picolyl chloride of the Formula B-8.

Chart C depicts a method of preparing the 2-mercaptobenzimidazoles used in Chart A. A substituted phenylenediamine compound of the Formula C-1 (such compounds are well known and readily available or can be prepared by known means) is treated with potassium hydroxide and carbon disulfide to yield the Formula C-2 compound. This is also described in Example 4.

All of the compounds of this invention are prepared by the procedures described above.

Certain compounds of the present invention are preferred. Thus, compounds of the Formula I, wherein $R_1$ is hydrogen; X is $=S(O)$; $R_3$ is methyl or ethyl; $R_4$ is hydrogen, and $R_2$ is methylthio, ethylthio or propylthio are preferred. More preferred are compounds wherein $R_2$ is ethylthio. Thus, 2-[(4-ethylthio-3-methylpyridin-2-ylmethyl)sulfinyl]-benzimidazole (compound 7 of Table 1) and 2-[(4-ethylthio-3-ethylpyridin-2-ylmethyl)sulfinyl]-benzimidazole (compound 12 of Table 1) are preferred. 2-[(4-ethylthio-3-methylpyridin-2-ylmethyl)sulfinyl]-benzimidazole is the most preferred compound of this invention.

DESCRIPTION OF THE PREFERRED EMBODIMENTS

The present invention is seen more fully by the examples given below.

All of the compounds of the present invention are prepared using the procedures described in the Examples below. Some physical and chemical properties of some of the compounds of this invention are given in Table 1.

EXAMPLE 1

Procedure for the preparation of thio ethers

Refer to Chart A (conversion of A-1 to A-2 to A-3)

To a magnetically stirred 0.2–0.4M 95% ethanol solution of a Formula A-2 substituted α-picolyl chloride (one equivalent) is added one equivalent of a substituted 2-mercaptobenzimidazole of Formula A-1 and two equivalents of 10N sodium hydroxide. The contents are placed in a 70°–75° C. oil bath and stirring continued for 1 hour. The reaction is cooled to room temperature, diluted with chloroform, and the chloroform is successively washed with 1N sodium hydroxide, water and saturated brine. The chloroform solution is dried through sodium sulfate and concentrated invacuo. The residual crude product is used in most instances in the subsequent oxidation step without further purification. When necessary, the crude product can be purified by silica gel column chromatography and/or crystallization from common organic solvents. The chromatography is preferably undertaken using a 1:2 mixture of acetone:methylene chloride with a trace of triethylamine although a 2% methanol in ethyl acetate solution, or various ethyl acetate:ether mixtures are also employed. Crystallization, when necessary, is preferably undertaken using mixtures of: ethyl acetate/ether/Skellysolve B (a commercial mixture of essentially n-hexane); ethyl acetate/diethyl ether; and the like.

EXAMPLE 2

Procedure for the Oxidation of Thioethers

Refer to Chart A (conversion of A-3 to A-4)

To a magnetically stirred 0.4–0.5M chloroform solution of a thioether (one equivalent), cooled in a 0°–5° C. ice-water bath, is added in a few portions one equivalent of meta-chloroperbenzoic acid. Stirring is continued at 0°–5° C. for 5–10 minutes. The contents are diluted with chloroform, washed with saturated sodium bicarbonate and saturated brine and the chloroform solution is dried through sodium sulfate. Removal of the solvent gives the crude product which is purified by silica gel column chromatography and/or crystallization as described in Example 1.

EXAMPLE 3

Preparation of Substituted α-picolyl chlorides

Refer to Chart B.

A. Conversion of B-1 to B-2.

To a magnetically stirred solution of the Formula B-1 2-methyl pyridine (approximately 0.40 mmol) in 230 ml of acetic acid is added 38 ml of 30% hydrogen peroxide. The contents are placed in an oil bath maintained at 70°–80° C. After 2.5 hours, an additional 23 ml of hydrogen peroxide is added and heating continued for an additional 6 hours. The reaction flask is then cooled in an ice-acetone bath and 327 ml of a 45% potassium hydroxide solution is slowly added. The aqueous solution is thoroughly extracted with chloroform, dried over sodium sulfate, and the methylene chloride is removed in vacuo. The residual solid is dried in vacuo at 50° C. to afford the Formula B-2 product which is used without further purification.

B. Conversion of B-2 to B-3.

The Formula B-2 N-oxide (approximately 0.50 mmol) is melted in a 60° C. oil bath. To this melt is slowly and cautiously added 146 ml of concentrated sulfuric acid with ice-bath-cooling. The solution is cooled in an ice-bath and 76 ml of fuming nitric acid (90%) is added dropwise over a 10 minute period. The cooling bath is removed when the solution temperature remains constant (22° C.). The contents are then placed in an oil bath initially at 30° C. and the temperature is gradually increased to 95° C. over a period of 2 hours. Heating is continued at 95° C. for 2 hours, the reaction is cooled to 10° C. in a cooling bath, poured into 1 liter of crushed ice and neutralized to pH 3 with 650 ml of 10N sodium hydroxide. The solid that appears is filtered, washed with 500 ml of water, dried at 50° C. in vacuo and recrystallized from ethyl acetate-ether to give the Formula B-3 product. The filtrate is extracted with chloroform and dried over sodium sulfate.

C. Conversion of B-3 to B-4.

To a magnetically stirred solution of 25 ml of acetyl chloride is added approximately 27.50 mmol of Formula B-3 compound as a solid in several portions. After addition, the contents are heated in a 100° C. oil bath for 10 minutes. The solution is cooled to 25° C., poured into 200 ml of crushed ice and treated with 48 g of solid potassium carbonate to pH 9. The aqueous solution is extracted with chloroform, dried over sodium sulfate and concentrated in vacuo to give the crude product which is chromatographed on 160 g of silica gel and eluted with methylene chloride-acetone (2:1).

D. Conversion of B-4 to B-5.

To a magnetically stirred suspension of sodium hydride (60% oil dispersion, 0.702 g., 17.54 mmol) in 20 ml of DMF is added approximately 17.54 mmol), of the $R_2H$ compound. Stirring is continued at 25° C. for 0.5 hours. At the end of this period, approximately 11.70 mmol of the B-4 compound in dimethylformamide (DMF) is added and this reaction is heated in a 100° C. oil bath for 1 hour. The contents are poured into 75 ml of ice water, extracted thoroughly with chloroform, the chloroform extracts are washed with saturated brine, and the mixture is dried over sodium sulfate and concentrated in vacuo. The crude product is chromatographed on 175 g of silica gel and eluted with chloroform:methanol (95:5).

E. Conversion of B-5 to B-6.

Approximately 15.82 mmol of the B-5 compound are treated with 9 ml of acetic anhydride and heated in a 100° C. oil bath for 15 minutes. The contents are cooled to 25° C. and teated with 75 ml of saturated sodium carbonate solution and then with solid sodium carbonate and extracted thoroughly with chloroform or ethyl acetate. The organic phase is washed with sodium carbonate solution, saturated brine, dried over sodium sulfate and concentrated in vacuo to afford the B-6 compound which is used without further purification.

F. Conversion of B-6 to B-7.

Approximately 13.21 mmol of the B-6 compound in 28 ml of 10% hydrochloric acid are heated in an 100° C. oil bath for 0.5 hours. The reaction is worked up in the same manner as described in Part E. The crude product is chromatographed on 150 g of silica gel and eluted with methylene chloride-acetate (4:1) to afford the Formula B-7 product.

G. Conversion of B-7 to B-8.

To approximately 2.50 mmol of the B-7 compound in 10 ml of methylene chloride are added 202 μl (2.63 mmol) of methanesulfonyl chloride and 381 μl (2.75 mmol) of triethylamine. Stirring is continued at 25° C. for 48 hours. The solution is then diluted with methylene chloride, washed with water and then saturated brine, dried over sodium sulfate and concentrated in vacuo to give the B-8 product which is used without further purification.

EXAMPLE 4

Preparation of substituted 2-mercaptobenzimidazoles

Refer to Chart C (conversion of C-1 to C-2).

To a magnetically stirred solution of the Formula C-1 diamine, as the hydrochloride (0.115 mol) in 400 ml of ethanol-water (4:1) is added 2 molar equivalents of 85% potassium hydroxide solution and 20 ml of carbon disulfide. The contents are warmed in a 75°–80° C. oil bath for 2.5 hours and the solvent is removed in vacuo. To the residual thick slurry is added 200 ml of water, the contents heated to boiling, and 95% ethanol is added until a transparent solution is obtained. The solution is filtered, the filtrate is allowed to stand at 25° C. and the resulting crystalline solid is collected, and washed with water-ethanol. Drying in vacuo affords the desired product.

TABLE I

| # | Compound Name | $R_1$ | X | $R_3$ | $R_2$ | $R_4$ | Mass Spectra[1] | Melting Point (°C.) | Yield (%) | Color |
|---|---|---|---|---|---|---|---|---|---|---|
| 1 | 2-[(4-methylthio-3-ethylpyridin-2-ylmethyl)sulfinyl]-5-methoxybenzimidazole | $CH_3O-$ | $=S(O)$ | $C_2H_5-$ | $-SCH_3$ | $H-$ | 400.0556 C 400.0559 F $[M + K]^+$ | 141–142 | 63 | pale green |
| 2 | 2-[(4-methylthio-3-ethylpyridin-2-ylmethyl)sulfinyl]-benzimidazole | $H-$ | $=S(O)$ | $C_2H_5-$ | $-SCH_3$ | $H-$ | 370.0450 C 370.0470 F $[M + K]^+$ | 154 | 53 | pale green |
| 3 | 2-[(4-methylthio-3-ethylpyridin-2-yl-methyl)sulfinyl]-5-trifluoromethylbenzimidazole | $F_3C-$ | $=S(O)$ | $C_2H_5-$ | $-SCH_3$ | $H-$ | 438.0324 C 438.0339 F $[M + K]^+$ | 145–147 | 50 | gray |
| 4 | 2-[(4-morpholinyl-3-ethylpyridin-2-ylmethyl)sulfinyl]-benzimidazole | $H-$ | $=S(O)$ | $C_2H_5$ | morpholinyl | $H-$ | 371.1542 C 371.1554 F $[M + H]^+$ | 146–147 | | off white |
| 5 | 2-[(4-ethylthio-3-ethylpyridin-2-yl-methyl)sulfinyl]-5-trifluoromethylbenzimidazole | $F_3C-$ | $=S(O)$ | $C_2H_5-$ | $-SC_2H_5$ | $H-$ | 452.0480 C 452.0500 F $[M + K]^+$ | 139–141 | 50 | |
| 6 | 2-[(4-ethylthio-3-methylpyridin-2-ylmethyl)sulfinyl]-5-methoxybenzimidazole | $CH_3O-$ | $=S(O)$ | $CH_3-$ | $-SC_2H_5$ | $H-$ | 400.0556 C 400.0563 F $[M + K]^+$ | | 76 | tan |
| 7 | 2[(4-ethylthio-3-methylpyridin-2-yl methyl)sulfinyl]-benzimidazole | $H-$ | $=S(O)$ | $CH_3-$ | $-SC_2H_5$ | $H-$ | 370.0450 C 370.0455 F $[M + K]^+$ | 148–151 | 58 | white |
| 8 | 2-[(4-benzyloxy-3-ethylpyridin-2-yl-methyl)sulfinyl]-benzimidazole | $H-$ | $=S(O)$ | $C_2H_5-$ | benzyloxy | $H-$ | 460.1097 C 460.1091 F $[M + K]^+$ | 145–147 | | white |
| 9 | 2-[(4-benzyloxy-3-ethylpyridin-2-yl-methyl)sulfinyl]-5-methoxybenzimidazole | $CH_3O-$ | $=S(O)$ | $C_2H_5-$ | benzyloxy | $H-$ | 460.1097 C 460.1091 F $[M + K]^+$ | 148–152 | 77 | pale yellow |
| 10 | 2-[(4-benzoyloxy-3-ethylpyridin-2-yl methyl)thio]benzimidazole | $H-$ | $=S$ | $C_2H_5-$ | benzyloxy | $H-$ | 376.1483 C 376.1476 F $[M + H]^+$ | | 74 | white |
| 11 | 2-[(4-benzyloxy-3-ethylpyridin-2-yl-methyl)thio]-5-methoxybenzimidazole | $CH_3O-$ | $=S$ | $C_2H_5-$ | benzyloxy | $H-$ | 406.1489 C 406.1580 $[M+]$ | | 75 | white |
| 12 | 2-[(4-ethylthio-3-ethylpyridin-2-yl-methyl)sulfinyl]-benzimidazole | $H-$ | $=S(O)$ | $C_2H_5-$ | $-SC_2H_5-$ | $H-$ | 384.0607 C 384.0591 F $[M + K]^+$ | 153–154 | 57 | white |
| 13 | 2-[(4-ethylthio-3-ethylpyridin-2-yl-methyl)sulfinyl]-5-methoxybenzimidazole | $CH_3O-$ | $=\dot{S}(O)$ | $C_2H_5-$ | $-SC_2H_5$ | $H-$ | 452.0271 C 452.0257 F $[M + 2K - H]^+$ | 111–114 | 83 | off white |
| 14 | 2-[(4-methoxy-3- | $H-$ | $=S$ | $C_2H_5-$ | $-OCH_3$ | $H-$ | 338.0729 C | | 80 | white |

TABLE I-continued

| # | Compound Name | $R_1$ | X | $R_3$ | $R_2$ | $R_4$ | Mass Spectra[1] | Melting Point (°C.) | Yield (%) | Color |
|---|---|---|---|---|---|---|---|---|---|---|
| | ethylpyridin-2-yl-methyl)thio]-benzimidazole | | | | | | 338.0732 F $[M + K]^+$ | | | |
| 15 | 2-[(4-methoxy-3-ethylpyridin-2-yl-methyl)sulfinyl]-benzimidazole | H— | =S(O) | $C_2H_5$— | —$OCH_3$ | H— | 354.0679 C 354.0685 F $[M + K]^+$ | 136–137.5 | 85 | tan |
| 16 | 2-[(4-methoxy-3-ethylpyridin-2-yl-methyl)sulfinyl]-5-methoxybenzimidazole | $CH_3O$— | =S(O) | $C_2H_5$— | —$OCH_3$ | H— | 384.0784 C 384.0776 F $[M + K]^+$ | 83–87 | 93 | pale white |
| 17 | 2-[(4-methoxy-3-ethylpyridin-2-yl-methyl)thio]-5-methoxybenzimidazole | $CH_3O$— | =S | $C_2H_5$— | —$OCH_3$ | H— | 368.0835 C 368.0845 F $[M + K]^+$ | | 79 | white |
| 18 | 2-[(4-benzloxypyridin-2-ylmethyl)-sulfinyl]-5-methoxy-benzimidazole | $CH_3O$— | =S(O) | H— | benzyloxy | H— | 393.1147 C 393.1156 F $[M+]$ | 74–44 | 74 | white |
| 19 | 2-[(4-piperidinyl-5-ethylpyridin-2-yl-methyl)sulfinyl]-5-methoxybenzimidazole | $CH_3O$— | =S(O) | H— | piperidinyl | $C_2H_5$— | 398.1176 C 398.1767 F $[M+]$ | 99–100 | 63 | |
| 20 | 2-[(4-morpholinyl-5-ethylpyridin-2-yl-methyl)-sulfinyl]-5-methoxybenzimidazole | $CH_3O$— | =S(O) | H— | morpholinyl | $C_2H_5$— | 400.1569 C 400.1566 F $[M+]$ | 100–102 | 71 | |
| 21 | 2-[(4-N,N—dimethyl-amino-5-ethylpyridin-2-ylmethyl)sulfinyl]-5-methoxybenzimidazole | $CH_3O$— | =S(O) | H— | —$N(CH_3)_2$ | —$C_2H_5$ | 451.0608 C 451.0604 F $[M+]$ | 138 | 50 | rust |
| 22 | 2-[(4-phenylthio-3,5-dimethylpyridin-2-yl-methyl)sulfinyl]-5-methoxybenzimidazole | $CH_3O$— | =S(O) | $CH_3$— | phenylthio | $CH_3$— | 423.1075 C 423.1098 F $[M+]$ | | 81 | white |
| 23 | 2-[(4-phenylthio-3,5-dimethylpyridin-2-yl-methyl)thio]-5-methoxy-benzimidazole | $CH_3O$— | =S | $CH_3$ | phenylthio | $CH_3$— | 407.1126 C 407.1132 F $[M+]$ | | 72 | white |
| 24 | 2-[(4-ethylthio-3,5-dimethylpyridin-2-yl-methyl)sulfinyl]-5-methoxybenzimidazole | $CH_3O$— | =S(O) | $CH_3$— | —$SC_2H_5$ | $CH_3$— | 375.1075 C 375.1079 F $[M+]$ | 137–138 | 67 | white |
| 25 | 2-[(4-ethylthio-3,5-dimethylpyridin-2-yl-methyl)thio]-5-methoxybenzimidazole | $CH_3O$— | =S | $CH_3$— | —$SC_2H_5$ | $CH_3$— | 359.1126 C 359.1137 F $[M+]$ | | 70 | golden |
| 26 | 2-[(4-phenylthio-5-ethylpyridin-2-yl-methyl)sulfinyl]-5-methoxybenzimidazole | $CH_3O$— | =S(O) | H— | phenylthio | —$C_2H_5$ | 423.1075 C 423.1111 F $[M+]$ | | 88 | white |
| 27 | 2-[(4-phenylthio-5-ethylpyridin-2-yl-methyl)thio]-5-methoxy-benzimidazole | $CH_3O$— | =S | H— | phenylthio | —$C_2H_5$ | 407.1126 C 407.1140 F $[M+]$ | | 68 | white |
| 28 | 2-[(4-phenylthio-pyridin-2-ylmethyl)-sulfinyl]-5-methoxy-benzimidazole | $CH_3O$— | =S(O) | H— | phenylthio | —H | 395.0762 C 395.0789 F $[M+]$ | | 76 | white |
| 29 | 2-[(4-phenylthio-pyridin-2-ylmethyl)-thio]-5-methoxybenz-imidazole | $CH_3O$— | =S | H— | phenylthil | —H | 379.0813 C 379.0803 F $[M+]$ | | 77 | white |
| 30 | 2-[(4-ethylthio-5-ethylpyridin-2-yl-methyl)sulfinyl]-5-methoxybenzimidazole | $CH_3O$— | =S(O) | H— | —$SC_2H_5$ | —$C_2H_5$ | 375.1075 C 375.1057 F $[M+]$ | 97–101 | 68 | white |
| 31 | 2-[(4-ethylthio-5-ethylpyridin-2-yl-methyl)thio-5-methoxy-benzimoidazole | $CH_3O$— | =S | H— | —$SC_2H_5$ | —$C_2H_5$ | 359.1126 C 359.1134 F $[M+]$ | 124–125 | 74 | cream |
| 32 | 2-[(4-ethylthio-pyridin-2-ylmethyl)-sulfinyl]-5-methoxy-benzimidazole | $CH_3O$— | =S(O) | H— | —$SC_2H_5$ | H— | 347.0762 C 347.0779 F $[M+]$ | 154–155 | 57 | white |
| 33 | 2-[(4-ethylthio-pyridin-2-ylmethyl)-thio]-5-methoxybenz-imidazole | $CH_3O$— | =S | H— | —$SC_2H_5$ | H— | 331.0813 C 331.0812 $[M+]$ | 130–132 | 65 | white |

TABLE I-continued

| # | Compound Name | $R_1$ | X | $R_3$ | $R_2$ | $R_4$ | Mass Spectra[1] | Melting Point (°C.) | Yield (%) | Color |
|---|---|---|---|---|---|---|---|---|---|---|
| 34 | 2-[(4-phenoxy-5-ethylpyridin-2-yl-methyl)sulfinyl]-5-methoxybenzimidazole | $CH_3O-$ | $=S(O)$ | $H-$ | phenoxy | $C_2H_5-$ | 407.1304 C 407.1318 F $[M^+]$ | | 67 | pink |
| 35 | 2-[(4-phenoxypyridin-2-ylmethyl)sulfinyl]-5-methoxybenzimidazole | $CH_3O-$ | $=S(O)$ | $H-$ | phenoxy | $H-$ | 379.0991 C 379.0988 F $[M^+]$ | | 68 | purple |
| 36 | 2-[(4-phenoxy-5-ethyl-pyridin-2-ylmethyl)-thio]-5-methoxybenz-imidazole | $CH_3O-$ | $=S$ | $H-$ | phenoxy | $-C_2H_5$ | 391.1354 C 391.1358 F $[M^+]$ | | 62 | white |
| 37 | 2-[(4-phenoxy-pyridin-2-ylmethyl)thio]-5-methoxybenzimidazole | $CH_3O-$ | $=S$ | $H-$ | phenoxy | $H-$ | 363.1041 C 363.1053 F $[M^+]$ | | 66 | color-less |
| 38 | 2-[(4-(2,6-dimethyl-phenoxy)-2-pyridinyl)-methylthio]-5-methoxy-benzimidazole | $CH_3O-$ | $=S$ | $H-$ | dimethyl-phenoxy | $H-$ | 391.1354 C 391.1366 F $[M^+]$ | | 55 | white |
| 39 | 2-[(4-(2,6-dimethyl-phenoxy)-2-pyridinyl)-methylsulfinyl]-5-methoxybenzimidazole | $CH_3O-$ | $=S(O)$ | $H-$ | dimethyl-phenoxy | $H-$ | 407.1304 C 407..1318 F $[M^+]$ | | 82 | pink |
| 40 | 5-methoxy-2-[[[4-(phenoxymethoxy)-2-pyridinyl]methyl]-thio]-1H—benzimido-zole | $CH_3O-$ | $=S$ | $H-$ | benzyloxy | $H-$ | 377.1197 C 377.1198 F $[M^+]$ | 149-151 | 75 | white |
| 41 | 5-methoxy-2-[[[4-[(3,4,5-trimethoxy-phenyl)methoxy]-2-pyridinyl]methyl]-thio]-1H—benzimido-zole | $CH_3O-$ | $=S$ | $H-$ | trimethoxy-benzyloxy | $H-$ | 467.1515 C 467.1485 $[M^+]$ | 66-70 | 80 | white |
| 42 | 5-methoxy-2-[[[4-[(3,4,5-trimethoxy-phenyl)methoxy]-2-pyridinyl]methyl]-sulfinyl]-1H—benz-imidazole | $CH_3O-$ | $=S(O)$ | $H-$ | trimethoxy-benzyloxy | $H-$ | 522.1085 C 522.1101 F $[M + K]^+$ | 70-72 | 88 | white |
| 43 | 2-[[[3-ethyl-4-[(phenylmethyl)-thiol-2-pyridinyl]-methyl]sulfinyl]-1H-benzimidazole | $H-$ | $=S(O)$ | $C_2H_5-$ | benzylthio | $H-$ | 408.1204 C 408.1226 F $[M + H]^{30}$ | 141-143 | 68 | white |
| 44 | 2-[[[3-ethyl-4-[(phenylmethyl)-thiol-2-pyridinyl]-methyl]sulfinyl-5-methoxy-1H—benzimi-dazole | $CH_3O-$ | $=S(O)$ | $C_2H_5$ | benzylthio | $H-$ | 476.0869 C 476.0888 F $[M + K]^+$ | 69-74 | 75 | gray |
| 45 | 2-[[[4-(butylthio)-3-ethyl-2-pryidinyl]-methyl]sulfinyl]-1H—benzimidazole | $H-$ | $-S(O)$ | $C_2H_5$ | butylthio | $H-$ | 374.1361 C 374.1389 F $[M + H]^+$ | 125-127 | 60 | white |
| 46 | 2-[[[4-(butylthio)-3-ethyl-2-pyridinyl]-methyl]sulfinyl]-5-methoxy-1H—benzimi-dazole | $CH_3O-$ | $-S(O)$ | $C_2H_5-$ | butylthio | $H-$ | 404.1466 C 404.1488 F $[M + H]^+$ | 92-96 | 58 | pale green |
| 47 | 2-[[[2-ethyl-4-(propylthio)-2-pyridinyl]methyl]-sulfinyl]-1H—benz-imidazole | $H-$ | $=S(O)$ | $C_2H_5$ | propylthio | $H-$ | 398.0763 C 398.0782 F $[M + K]^+$ | 132-133 | 61 | white |
| 48 | 2-[[[3-ethyl-4-(propylthio)-2-pyridinyl]methyl]-sulfinyl-5-methoxy-1H—benzimidazole | $CH_3O-$ | $=S(O)$ | $C_2H_5-$ | propylthio | $H-$ | 428.0869 C 428.0857 F $[M + K]^+$ | 130-133 | 62 | white |
| 49 | 2-[[[3-methyl-4-(methylthio)-2-pyridinyl]methyl]-sulfinyl]-1H—benz-imidazole | $H-$ | $=S(O)$ | $CH_3$ | methylthio | $H-$ | 356.0294 C 356.0313 F $[M + K]^+$ | 166.0-166.5 | 61 | white |
| 50 | 2-[[[3-methyl-4-[(1-methylethyl)-thio-2-pyridinyl]-methyl]sulfinyl]-1H—benzimidazole | $H-$ | $=S(O)$ | $CH_3-$ | isopropyl-thio | $H-$ | 346.1048 C 346.1048 F $[M + H]^+$ | 153-154 | 69 | tan |

TABLE I-continued

| # | Compound Name | $R_1$ | X | $R_3$ | $R_2$ | $R_4$ | Mass Spectra[1] | Melting Point (°C.) | Yield (%) | Color |
|---|---|---|---|---|---|---|---|---|---|---|
| 51 | 2-[[[4-[(1,1-di-methylethyl)thio]-3-methyl-2-pyridinyl]-methyl]sulfinyl]-1H—benzimidazole | H— | =S(O) | $CH_3$— | t-butylthio | H— | 398.0763 C 398.0775 F $[M + K]^+$ | 115–118 | 50 | blue |
| 52 | 2-[[[4-(ethylthio)-3-methyl-2-pyridinyl]-methyl]thiol-1H—benzimidazole | H— | =S | $CH_3$— | ethylthio | H— | 316.0942 C 316.0931 F $[M + H]^+$ | 158–159 | 62 | white |
| 53 | 2-[[[3-methyl-4-(2-propenylthio)-2-pyridinyl]methyl]-sulfinyl]-1H—benzimidazole | H— | =S(O) | $CH_3$— | propenyl-thio | H— | 344.0891 C 344.0906 F $[M + H]^+$ | 150–151 | 69 | white |
| 54 | 2-[[[3-n-propyl-4-(ethylthio)-2-pyridinyl]methyl-sulfinyl-1H—benzimidazole | H | =S(O) | n-propyl | ethylthio | H— | 398.0763 C 398.0749 F $[M + K]^+$ | 118–120 | 60 | purple |
| 55 | 2-[[[3-n-propyl-4-(methylthio)-2-pyridinyl]methyl-sulfinyl-1H—benzmidazole | H | =S(O) | n-propyl | methylthio | H— | 384.0607 C 384.0591 F $[M + K]^+$ | 110–112 | 63 | gray |
| 56 | 2-[[(4-cyclohexyl-thio]-3-methyl-2-pyridinyl]methyl]sulfinyl]-1H—benzimidazole | H | =S(O) | $CH_3$ | 4-cyclo-hexylthio | H— | 424.092 C 424.095 F | 142–144 | 44 | tan |

[1] Mass spectralanalysis calculated using fast-atom bombardment (FAB) "C" means calculated result, "F" indicates result found. The bracketed material indicates the ion fragment measured.

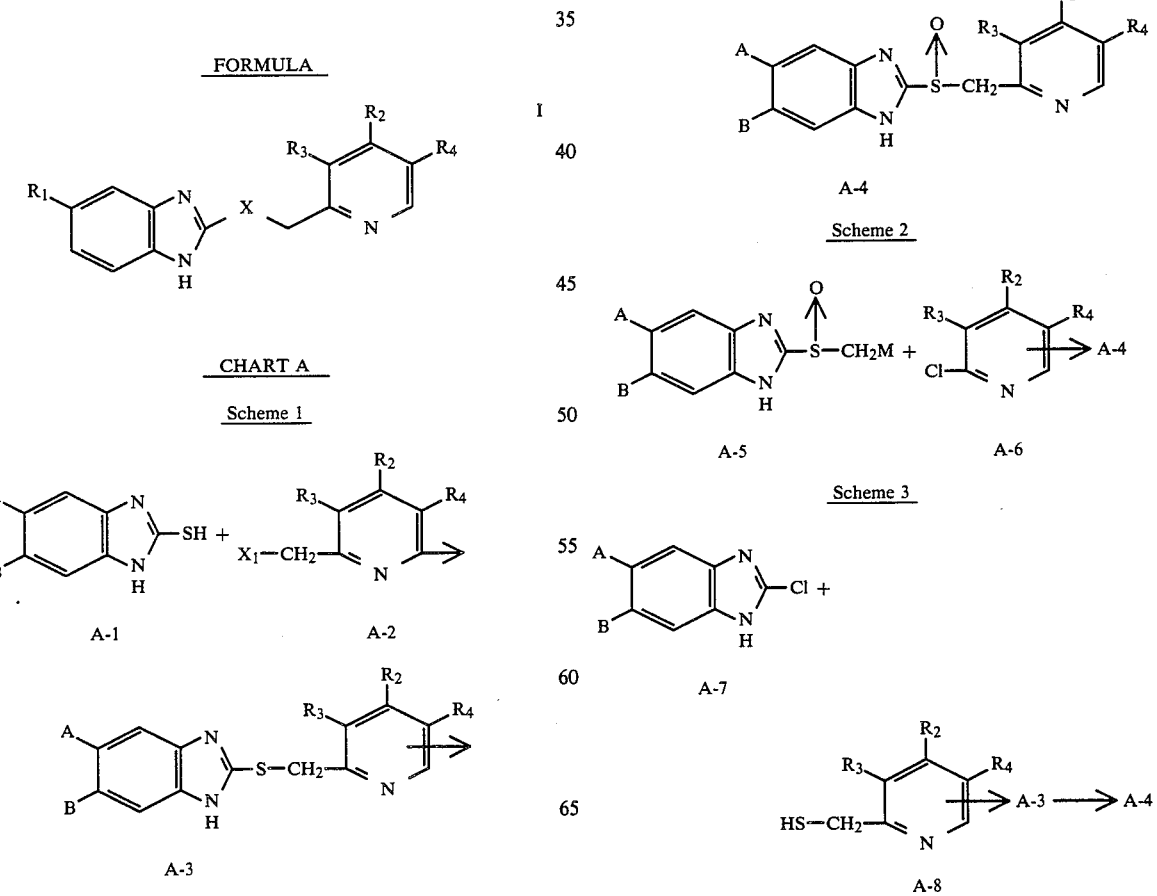

FORMULA I

CHART A

Scheme 1

Scheme 2

Scheme 3

CHART A

Scheme 4

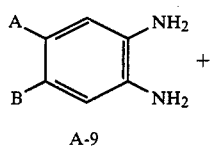

A-9

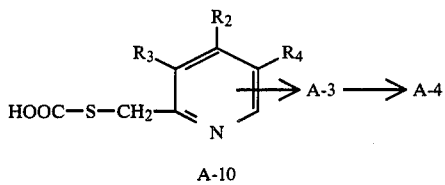

A-10

CHART B

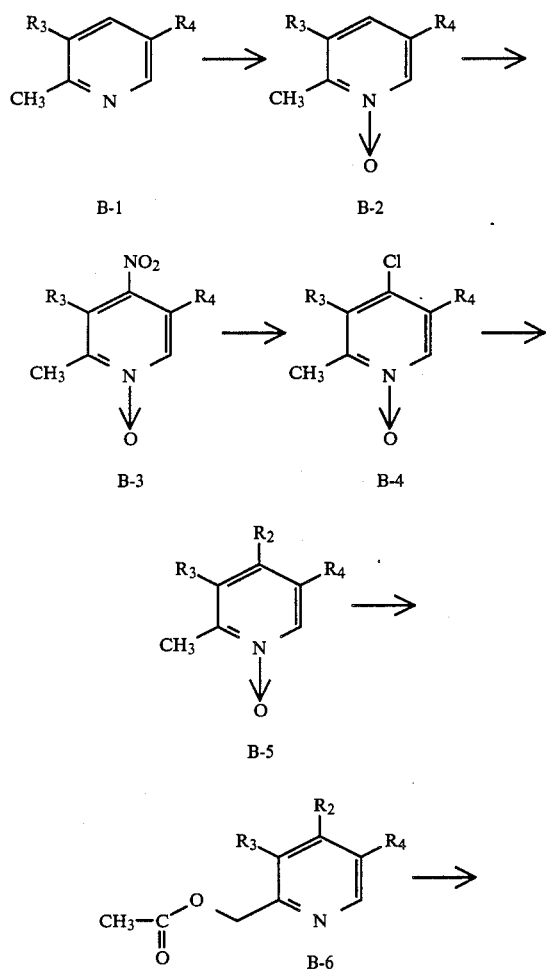

CHART B (continued)

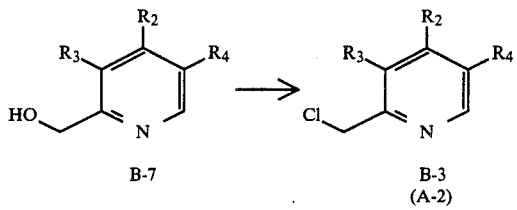

CHART C

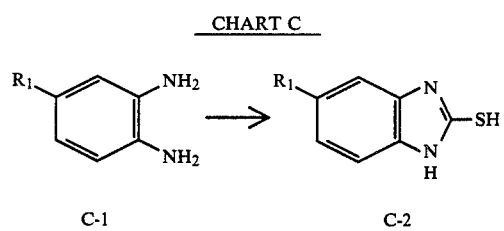

I claim:

1. A compound of the formula I:

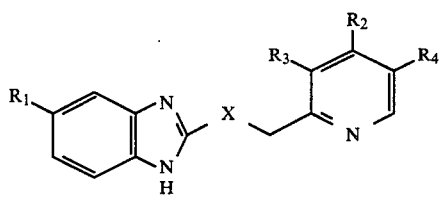

wherein X is
(a) =S, or
(b) =SO;
wherein $R_1$ is
(a) hydrogen,
(b) methyl,
(c) methoxy, or
(d) trifluoromethyl;
wherein $R_2$ is
(a) —$N(R_4)_2$
(b) 1-piperidinyl,
(c) 4-morpholinyl,
(d) 4-methyl-piperazin-1-yl, or
(e) 1-pyrrolidinyl;
wherein $R_3$ and $R_4$ are the same or different and are
(a) hydrogen, or
(b) $(C_1-C_4)$alkyl.

2. A compound of claim 1, selected from the group consisting of:
2-[(4-morpholinyl-3-ethylpyridin-2-ylmethyl)sulfinyl]-5-trifluoromethylbenzimidazole,
2-[(4-piperidinyl-5-ethylpyridin-2-ylmethyl)sulfinyl]-5-methoxybenzimidazole,
2-[(4-morpholinyl-5-ethylpyridin-2-ylmethyl)sulfinyl]-5-methoxybenzimidazole, and
2-[(4-N,N-dimethylamino-5-ethylpyridin-2-ylmethyl)-sulfinyl]-5-methoxybenzimidazole.

* * * * *